United States Patent
Stutz et al.

(10) Patent No.: US 9,644,622 B2
(45) Date of Patent: May 9, 2017

(54) MEMBRANE PUMP WITH AIR RELEASE VALVE

(71) Applicant: Medela Holding AG, Baar (CH)

(72) Inventors: Alex Stutz, Baar (CH); Beda Weber, Sins (CH); Erich Pfenninger, Ebikon (CH)

(73) Assignee: Medela Holding AG, Baar (CH)

( * ) Notice: Subject to any disclaimer, the term of this patent is extended or adjusted under 35 U.S.C. 154(b) by 693 days.

(21) Appl. No.: 13/936,064

(22) Filed: Jul. 5, 2013

(65) Prior Publication Data

US 2013/0294942 A1 Nov. 7, 2013

Related U.S. Application Data

(63) Continuation of application No. 11/662,683, filed on Mar. 12, 2007, now Pat. No. 8,512,010.

(30) Foreign Application Priority Data

Sep. 20, 2004 (CH) ...................................... 1541/04

(51) Int. Cl.
*F04B 43/00* (2006.01)
*F04B 45/04* (2006.01)
(Continued)

(52) U.S. Cl.
CPC ........... *F04B 43/00* (2013.01); *A61M 1/0072* (2014.02); *F04B 43/0054* (2013.01);
(Continued)

(58) Field of Classification Search
CPC ...... F04B 7/0076; F04B 7/0088; F04B 39/08; F04B 39/102; F04B 39/1073–39/1086;
(Continued)

(56) References Cited

U.S. PATENT DOCUMENTS

| 1,847,658 A | 3/1932 | Lasker | |
| 3,425,444 A | * 2/1969 | Jones | ................... F16K 17/0433 137/469 |
| 4,503,887 A | * 3/1985 | Johnson | ................ F16K 31/402 137/601.13 |
| 4,583,970 A | 4/1986 | Kirchner | |
| 4,651,778 A | * 3/1987 | Pernat | ...................... A01J 5/048 137/489 |
| 4,673,388 A | * 6/1987 | Schlensog | ............. A61M 1/005 601/14 |
| 4,865,525 A | 9/1989 | Kern | |
| 4,886,494 A | * 12/1989 | Morifuji | ............. A61M 1/0023 604/347 |
| 5,083,746 A | * 1/1992 | Fransworth | ......... F16K 31/0672 251/129.17 |
| 6,090,065 A | * 7/2000 | Giles | ....................... A61M 1/06 604/315 |
| 6,355,012 B1 | 3/2002 | Nuesch | |
| 6,786,468 B2 | * 9/2004 | Schroeder | ........... F16K 31/0672 251/129.17 |

(Continued)

FOREIGN PATENT DOCUMENTS

EP 0520135 12/1992
EP 1221319 7/2002
(Continued)

OTHER PUBLICATIONS

International Search Report dated Jan. 9, 2009.
International Search Report dated Aug. 31, 2009.

*Primary Examiner* — Charles Freay
*Assistant Examiner* — Joseph Herrmann
(74) *Attorney, Agent, or Firm* — McDonnell Boehnen Hulbert & Berghoff LLP (57) ABSTRACT

A suction pump, in particular a breast pump, comprises a bleed valve with a bleed opening, a bleed body which seals the bleed opening and an operating means for operating the bleed body. The bleed body may be operated such that upon opening the valve initially only a partial region of the bleed opening is released and subsequently a greater part thereof or the whole bleed opening is released. The suction pump provides a large functionality with the smallest size and, furthermore, is cheap to produce and easily assembled.

20 Claims, 6 Drawing Sheets (51) Int. Cl.
  *F04B 45/047* (2006.01)
  *F04B 49/03* (2006.01)
  *F04B 49/10* (2006.01)
  *F16K 31/06* (2006.01)
  *A61M 1/00* (2006.01)
  *A61M 1/06* (2006.01)

(52) U.S. Cl.
  CPC ............ *F04B 45/04* (2013.01); *F04B 45/047* (2013.01); *F04B 49/03* (2013.01); *F04B 49/10* (2013.01); *A61M 1/0074* (2013.01); *A61M 1/06* (2013.01); *F16K 31/0672* (2013.01)

(58) Field of Classification Search
  CPC ...... F04B 39/1093; F04B 43/04; F04B 49/03; F04B 49/10; F04B 43/00; F04B 43/0054; F04B 45/04; F04B 45/047; A61M 1/06; A61M 1/0023; A61M 1/0035; A61M 1/005; A61M 1/0031; A61M 1/0033; A61M 5/14224; A61M 1/0072; A61M 1/0074; A61M 39/22; A61M 39/242; F16K 31/0672
  USPC .................................................. 251/129.17
  See application file for complete search history.

(56) References Cited

U.S. PATENT DOCUMENTS 7,381,197 B2 * 6/2008 Kelly ...................... A61M 1/06
  604/74
7,637,284 B1 * 12/2009 Feldmeier ............... F16K 11/20
  137/883

FOREIGN PATENT DOCUMENTS

| JP | 07-136245 | 5/1995 |
| JP | 2002-035111 | 2/2002 |
| WO | 00/41745 | 7/2000 |
| WO | 01/047577 | 7/2001 |
| WO | 03/057276 | 7/2003 |
| WO | 2004/069306 | 8/2004 |

* cited by examiner

MEMBRANE PUMP WITH AIR RELEASE VALVE

CROSS-REFERENCE TO RELATED APPLICATIONS

This application is a continuation of U.S. application Ser. No. 11/662,683 filed Mar. 12, 2007, which claims the benefit of Swiss Patent Application No. 1541/04 filed Sep. 20, 2004, the contents of which are fully incorporated herein by reference.

TECHNICAL FIELD

The invention relates to a suction pump and a method for operating a suction pump.

BACKGROUND

Suction pumps are known for a wide variety of applications. However, they can preferably be used in breast pump devices for pumping off breast milk, or as drainage pumps for suctioning off body fluids.

There are suction pumps in closed systems which at all times move the same air within the pump chamber. However, open pump systems are also known with an air release valve which can be opened cyclically via an electromagnet.

The requirements placed on these suction pumps, in particular when they are used as breast pumps, are quite high. They should be as powerful as possible but, at the same time, relatively small. Particularly in their use as breast pumps, they should be able to operate with minimum maintenance and should be easy to clean.

SUMMARY

It is therefore an object of the invention to make available a suction pump and a method for operating a suction pump permitting the smallest possible design of the pump yet at the same time allowing short pump cycles.

In the method according to a preferred variant of the invention, an air release body, which closes an air release opening of the air release valve, is at first only partially lifted. In this way, a smaller force is needed than if the whole air release opening is freed in a single step.

The means for actuating, in particular for lifting, the air release body can therefore be less powerful and can thus be made smaller. If an electromagnet is used as such a means, a relatively low-power type can be used. The reason is that, when pulling up or lifting the air release body, the electromagnet can at first apply less force than it does at the end of the movement. This initially available lower force, however, is sufficient to free a relatively small opening. It is therefore possible to use a relatively small and thus also inexpensive electromagnet. Moreover, the air release opening can be made relatively large. This ensures a rapid cancellation of the underpressure and, therefore, the desired functionality of the pump.

The pump easily reaches 120 cycles per minute. However, it can also operate optimally at a cycle rate of 50-72 cycles per minute. The first cycle rate is particularly suitable for stimulation, the second one for expression of breast milk.

In a preferred variant of the method according to the invention, only an edge area of the air release body is at first removed from the air release opening. A minimal amount of force is needed if this edge area coincides with a corner of the air release body.

The air release body is preferably a membrane. The lifting of its edge area is made easier if the lifted edge area is less thick than the rest of the membrane. The air release opening is preferably polygonal, in particular square or triangular. The membrane too is preferably polygonal, preferably square or triangular.

To permit easier lifting of the membrane, a connecting pin can be secured to it or integrally formed on it, and this connecting pin is connected to an armature of the lifting magnet. This connecting pin is preferably situated in the edge area of the membrane that covers the air release opening. However, the membrane can also be designed with a raised flange, in which case the connecting pin is not arranged over the air release opening but instead on this raised flange.

If the connecting pin is designed so as to be movable relative to the membrane, it is possible to overcome any production-related or assembly-related tolerances. Errors in the angle of the electromagnet can also be compensated. Good results were achieved using a connecting pin which is formed integrally on an air release membrane made of silicone and which, by means of suitable thickening of the material, has sufficient stiffness. It can be formed thereon in a hinged manner. However, in a simple embodiment, the elasticity of the material of the connecting pin suffices to make it movable about its point of attachment.

In another embodiment, the air release body has a first subsidiary body and a second subsidiary body. A first subsidiary body closes the air release opening only partially, since it has an air release channel which creates a connection from the air release opening to the outside. This first subsidiary body including the air release channel can be closed by a second subsidiary body. When air is released, only the first subsidiary body is at first lifted, or distanced from the air release channel, such that only part of the air release opening is freed. The second subsidiary body can then also be distanced from it, such that the whole air release opening is now freed. In this second stage, the second subsidiary body can preferably be actuated jointly with the first subsidiary body.

Compared to this embodiment, the first embodiment mentioned, with the air release membrane that can be actuated in an edge area, has the advantage that it ensures leaktightness and thus, particularly when used in a breast pump, ensures there is no leakage of the pumped-off milk.

A further advantage of the abovementioned embodiments, particularly as regards the use of the membrane, is that no springs are needed, and the number of individual parts required can therefore be reduced. Since no spring has to be fitted, the work involved in assembling the pump is also reduced.

It is a further object of the invention to create a suction pump which can be put together as easily as possible.

The suction pump according to a preferred embodiment of the invention has an air release valve with an air release membrane, and this air release membrane and a vacuum membrane used to generate the vacuum are designed integrally in the form of a common membrane plate.

Arranging the air release valve and the vacuum membrane on the same plate means that these elements are less expensive to produce and are easier to assemble.

In a preferred embodiment, the pump comprises an upper housing part, a middle housing part and a lower housing part, with a membrane plate and a valve plate being arranged between the housing parts. This division means that several elements can be formed on the same structural part. In particular, the vacuum membrane needed to generate the underpressure, and the air release membrane needed to rapidly cancel the underpressure, can be formed integrally on the same structural part. Control flaps and valve flaps can also be formed integrally on a common structural part. Electric motor and electromagnet can be secured in the same housing part. By dividing the pump into several levels, preferably five levels, the number of individual parts can be reduced to a minimum without having to give up the complexity of the pump assembly. This not only reduces the outer dimensions of the pump assembly, but also minimizes the production and assembly costs.

A further advantage of this modular construction with several levels is that the pump can be cleaned by simple flushing, without having to be dismantled into its individual parts. By virtue of the exhaust leading to the outside, no sponge is needed. Such sponges are used in the prior art to absorb milk that has been sucked into the pump and also to attenuate noise. However, they take up space in the pump and tend to give rise to unpleasant odor.

This modular construction can also be used in a pump that does not have the abovementioned air release valve according to the invention.

It is a further object of the invention to make available a suction pump which has a safety valve and which cannot be inactivated by liquid, in particular milk, that has been sucked into the pump and has accumulated there.

The suction pump according to a preferred embodiment of the invention has a safety valve with a first stage which opens at a first underpressure, and with a second stage which opens at a second underpressure. The first underpressure is quantitatively lower than the second.

This two-stage design of the safety valve ensures that milk cannot get as far as the second stage. Since the first stage opens even in the event of a very slight deviation from the ideal underpressure, it will still open, in the event of clogging, when the underpressure is at a higher level, that is to say in an emergency situation. The second valve prevents the entire safety valve from opening at too small a deviation, but it still opens reliably in an emergency situation.

This two-stage safety valve can also be used in a pump that does not have the abovementioned air release valve according to the invention or the modular construction.

The suction pump according to the invention can therefore reduce the vacuum in a relatively short time and without too much force. The pump according to the invention is suitable for a wide variety of applications. It is suitable in particular as a breast pump for suctioning off breast milk and as a drainage pump for suctioning off body fluids. The pump assembly according to the invention is suitable in particular for use in a portable breast pump, as is described in particular in still to be published PCT/CH 2004/000061.

Further advantageous embodiments are set forth in the attached patent claims.

BRIEF DESCRIPTION OF THE DRAWINGS

The subject matter of the invention is explained below on the basis of preferred illustrative embodiments depicted in the attached drawings, in which.

DETAILED DESCRIPTION

Figure 1:
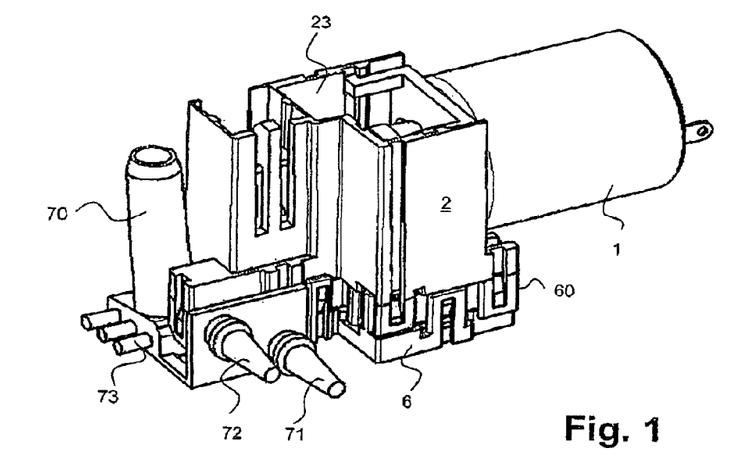
FIG. 1 shows a perspective view of the suction pump according to the invention without outer housing.

FIG. 1 shows a suction pump according to the invention, such as is suitable in particular for a breast pump device for pumping off human breast milk. However, the pump is also suitable for other applications, for example for drainage pumps for suctioning off body fluids.

Only the actual pump assembly is shown. This assembly is usually arranged in an outer housing. The figure does not show this outer housing and the electronics needed for actuating the pump, or any energy storage means, for example an accumulator or battery.

The pump has an extremely compact structure. One of its largest elements is an electric motor 1. It also has an upper housing part 2, a middle housing part 4 and a lower housing part 6, which can be plugged together. An attachment part 7 is also provided which is a component part of these housing parts or, as is the case here, is plugged onto them.

On the attachment part 7, there is at least one breast shield attachment piece 70 on which a connecting tube to a breast shield can be plugged. The attachment part 7 also comprises an exhaust 71. This exhaust 71 also leads out of the outer housing. An air release channel 72, also protruding from the outer housing, and spacer elements 73 are also present. The spacer elements 73 brace the pump assembly in relation to an outer housing in such a way that vibrations cannot be transmitted and a sufficient sound insulation is ensured.

Figure 2:
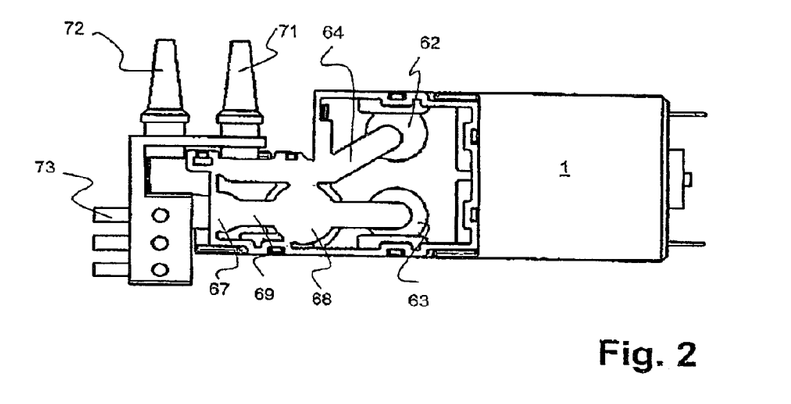
FIG. 2 shows a view of the suction pump according to FIG. 1 from below.

It will be seen from FIG. 2 how the individual attachments 70, 71, 72 are connected via individual channels to the individual areas of the pump.

Figure 3:
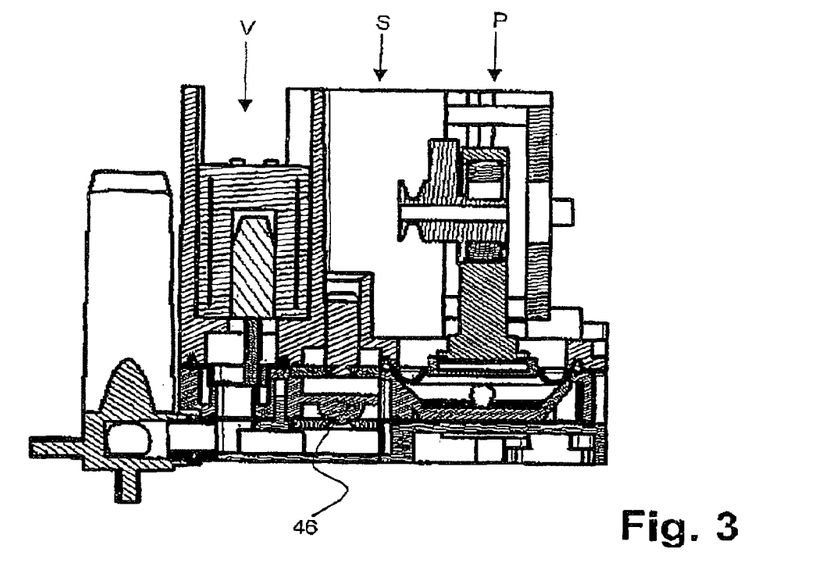
FIG. 3 shows a longitudinal section through the suction pump according to FIG. 1.

The longitudinal section shown in FIG. 3 through the pump, now without motor 1, shows that the pump, despite its compact design, is divided into three clearly distinguishable function areas: a pump unit P, an air release unit V and, arranged between these, a safety unit S. The structure of the pump can best be seen from an overview of FIGS. 3 and 4.

Figure 4:
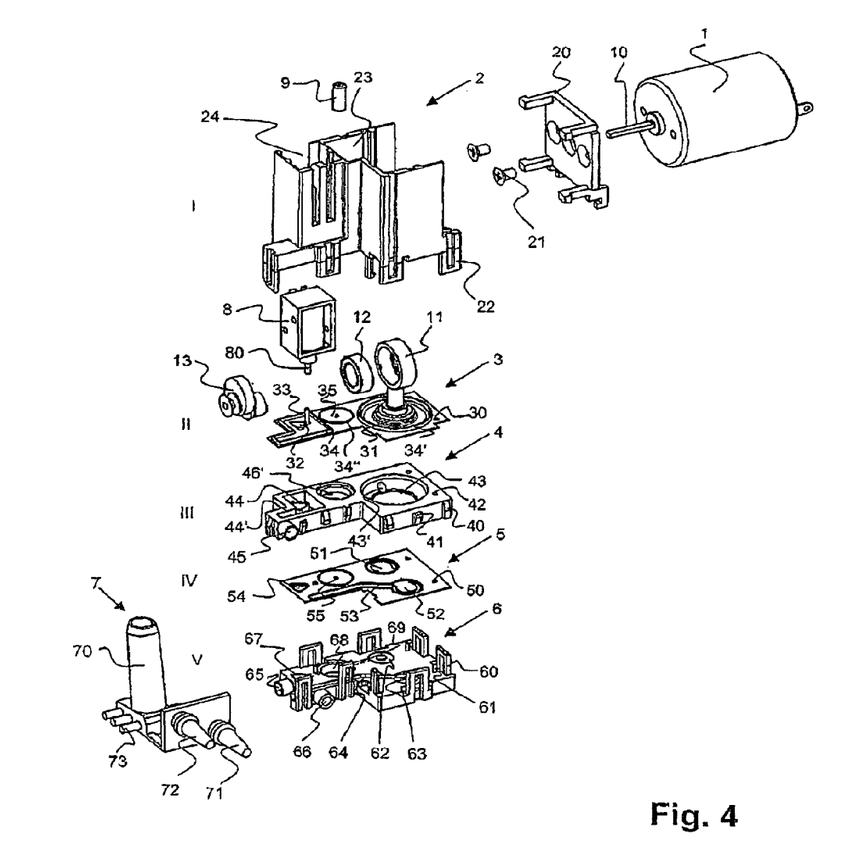
FIG. 4 shows an exploded view of the suction pump according to FIG. 1.

The pump unit P comprises a vacuum membrane 31 and inlet and outlet control flaps 51, 52 which, together with inlet and outlet openings 62, 63 and with a pump chamber opening 43', create a connection between a pump chamber 43 and a vacuum channel 69. The vacuum membrane 31 is connected to a drive shaft 10 of the electric motor 1 via a connecting rod 11, coupling piece 12, for example a ball bearing, and eccentric 13 and, by means of this motor 1, it can be lifted and lowered according to a predetermined rhythm or pump curve or according to a rhythm or pump curve that can be freely selected via a control system.

The air release unit V comprises an air release valve with an air release membrane 32, and an air release opening which can be closed tightly by the latter and is in the form of an air release membrane seat 44. The chamber 44' surrounding the air release membrane seat 44 is connected via an air release attachment 45 to the air release channel 72. The air release membrane seat 44 is open at the bottom, that is to say on the side directed away from the air release membrane 32, and adjoins a first air release opening 54 of the valve plate 5 and a second air release opening 67 of the lower housing part 6. This second air release opening 67 is connected via the vacuum channel 69 to a safety valve chamber 68 and to the inlet opening 62.

The air release membrane 32 is connected via a connecting pin 33 to an armature 80 of a lifting magnet or electromagnet 8. The electromagnet 8 lifts the air release membrane 32 and thus frees the air release membrane seat 44. By this means, air passes through the air release channel 72 and through the first and second air release openings 54, 67 into the vacuum channel 69, and the underpressure in the latter is reduced. This lifting and lowering of the air release membrane 32 also takes place according to a predetermined function or according to a function that can be freely selected via a control system, and which function is coordinated with the movement of the vacuum membrane 31. The movements of the vacuum membrane 31 and of the air release membrane 32 are preferably coordinated in such a way that a pump curve is obtained which is as described in WO 01/47577 and which is adapted to the needs of mother and child or imitates the natural sucking rhythm of a baby. The assembly functions in all positions, that is to say, for example, when it is lying or standing on a table or being carried. The vacuum generated is largely independent of how the assembly is spatially arranged.

The safety unit S comprises a safety valve. In the event of a malfunction or failure of the control electronics that coordinate the movement of the vacuum membrane 31 and of the air release membrane 32, this safety valve ensures that the level of the underpressure in the pump does not become too great and injure the mother's breast.

According to the invention, the safety unit S is designed with two stages. The first stage consists of a first safety membrane 55 and of a semispherical safety valve closure 46 which has a small lateral opening 46' and which presses on the first safety membrane 55. This first stage opens even at a low underpressure of about 120 mmHg.

The second stage comprises a second safety membrane 35 which is closed by means of an adjusting screw 9. Its limit value, at which it opens, can be modified by adjustment of the adjusting screw 9. According to the invention, it opens at a higher underpressure than the first stage, for example at about 290 mmHg.

If milk or another suctioned fluid accidentally gets into the pump, it settles in the area of the first stage and cannot pass through to the second stage via the chamber lying in between. At the very most, therefore, it can cover the first safety membrane 55. In this covered state, the latter possibly no longer opens at the preset value, but it always opens early enough to permit release. The second membrane always opens only when the limit value is actually exceeded and the pump has to be relieved. Since the second stage cannot be soiled, it always opens reliably.

The individual parts of the pump can best be seen in FIG. 4. This exploded view shows that the pump is divided into several levels I, II, III, IV and V, where parts of the pump unit P, of the safety unit S and of the air release unit V are arranged on common levels.

A first level I, which usually, but not necessarily, forms the uppermost level in the operating position, comprises the upper housing part 2, the aforementioned motor 1, and the electromagnet 8. The motor 1 is secured by fastening screws 21 onto a motor plate 20 of the upper housing part 2. The motor can be screwed onto the motor plate 20 and can likewise be plugged onto the pump assembly. The housing part 2 comprises a connecting rod chamber 23 which is used to receive the connecting rod 11, the ball bearing 12 connected thereto, and an eccentric with counterweight 13. The counterweight 13 does not necessarily have to be present. The upper housing part 2 also comprises a magnet chamber 24 which is separate from the connecting rod chamber 23 and in which the electromagnet 8 is secured. At its lower end, the upper housing part 2 has upper locking clips 22 which protrude downward.

The adjusting screw 9 for the second stage of the safety valve is also arranged adjustably in the upper housing part 2.

Figures 6, 7:
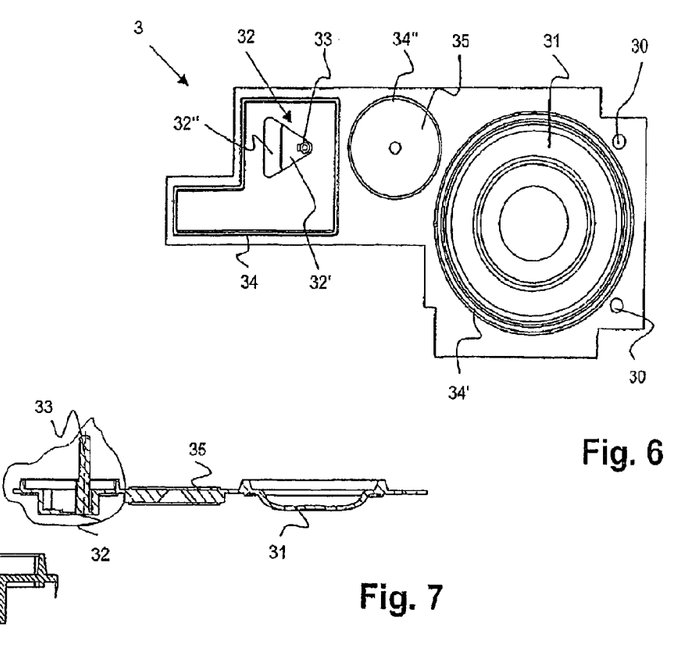
FIG. 6 shows a view of a membrane plate of the suction pump according to FIG. 1 from above.
FIG. 7 shows a longitudinal section through the membrane plate according to FIG. 6.
Figure 8:
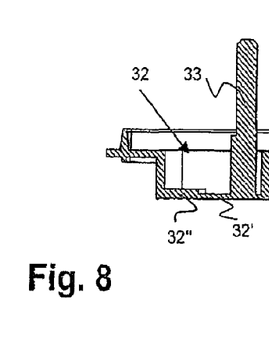
FIG. 8 shows an enlarged detail of the membrane plate according to FIG. 7.

The second level II is defined by a membrane plate 3 which extends at least approximately across the whole base surface of the upper housing part 2 and thus of the pump assembly. The membrane plate 3 is made of a flexible material, in particular silicone, and is relatively thin. It has centering holes 30 in its edge areas, and upper and lower sealing lips 34, 34', 34" which ensure an airtight and liquid-tight connection to the upper housing part 2 and middle housing part 4, respectively. The lower sealing lips can be seen in FIG. 7. The membrane plate 3 comprises the air release membrane 32, which is designed in the shape of a triangle. As can be seen in FIG. 6, the air release membrane 32 has a triangular basic shape. This triangle is divided into two subsidiary areas, where a first subsidiary area 32' again forms a triangle, and the second subsidiary area 32" is formed by the remaining part of the membrane and thus has a trapezoid shape. A first corner of the first subsidiary area 32' coincides with a corner of the air release membrane 32. An opposite side of the first subsidiary area 32' extends parallel to an opposite side of the air release membrane 32, and the two other sides of the triangle of the first subsidiary area 32' extend congruently with respect to the sides of the triangle of the air release membrane 32. The triangular first subsidiary area 32' is less thick than the second subsidiary area 32", as can be seen in FIGS. 7 and 8.

The connecting pin 33 is formed integrally on the free corner of the first subsidiary area 32'. As can also be seen from FIGS. 7 and 8, it projects upward at least approximately perpendicular to the plane of the membrane and is fixedly connected to the armature 80. The air release membrane 32 is surrounded by a first sealing lip 34.

The membrane plate 3 further comprises the vacuum membrane 31, which is connected to the connecting rod 11. The connecting rod 11 can be formed integrally on the vacuum membrane 31 by material thickening and can be composed of a two-component material. It can also be produced separately, however, and be connected to the membrane 31 during assembly. The vacuum membrane is sealed off from the upper and middle housing parts 2, 4 by means of a second sealing lip 34'.

The membrane plate 3 further comprises the second membrane 35 of the safety valve. The latter, as can best be seen in FIG. 7, has a v-shaped opening that widens toward the bottom and is sealed off from the upper and middle housing parts 2, 4 by means of a third sealing lip 34" that surrounds it.

The third level III is formed by the middle housing part 4. Like the upper and lower housing parts 2, 6, it is preferably made of a solid plastic material, for example POM (polyoxymethylene). The middle housing part 4 is panel-shaped and has a plane upper face and a plane lower face. On its side faces, it is provided with upwardly and downwardly directed catches 40, 41, respectively, the upper catches 40 engaging into the upper locking clips 22 of the upper housing part 2, and the lower catches 41 engaging into lower locking clips 60 of the lower housing part 6. Centering holes 42 are also present which are in alignment with the centering holes 30 of the membrane plate 3.

Two recesses, closed at the bottom and with small lateral connecting openings, are present in the middle housing part 4. One of these recesses forms the vacuum membrane seat 43 for the vacuum membrane and thus defines the pump chamber. A second of these recesses forms a safety closure 46 of the first safety stage. The chamber 44', with the membrane seat 44 arranged therein for the air release membrane 32, is also present in the middle housing part 4. This seat 44 has a triangular shape in this example. The chamber 44' is a recessed, h-shaped trough, the latter being connected to the air release attachment 45.

The fourth level IV in turn comprises a flexible plate, preferably of silicone. It is formed by a valve plate 5. This too has centering holes 50, at least one pair of these centering holes 50 being in alignment with the centering holes of the middle housing part 4 and of the membrane plate 3.

The valve plate 5 comprises a first control flap 51, which forms an inlet for the vacuum chamber. It further comprises a second control flap 52, which forms an outlet for the vacuum chamber. Leading away from the second control flap 52, there is a double sealing lip 53 which surrounds an upwardly open connecting channel 64 arranged in the lower housing part 6 and seals this connecting channel 64 at the top.

The first membrane 55 of the safety valve is also formed integrally in the valve plate 5. The latter also comprises the first air release opening 54, which ensures a connection between the air release membrane seat 44 and a second air release opening 67, which is arranged in the lower housing part 6. The individual elements of the valve plate 5 are in turn provided with upper and lower sealing lips to seal them relative to the middle and lower housing parts 4, 6. All the elements of the valve plate 5 are preferably produced integrally with the latter.

The fifth level V comprises the lower housing part 6 and the attachment part 7. These two parts can be formed by a single common part, or, as is shown here, they can be coupled to one another by plug connections.

Figure 5:
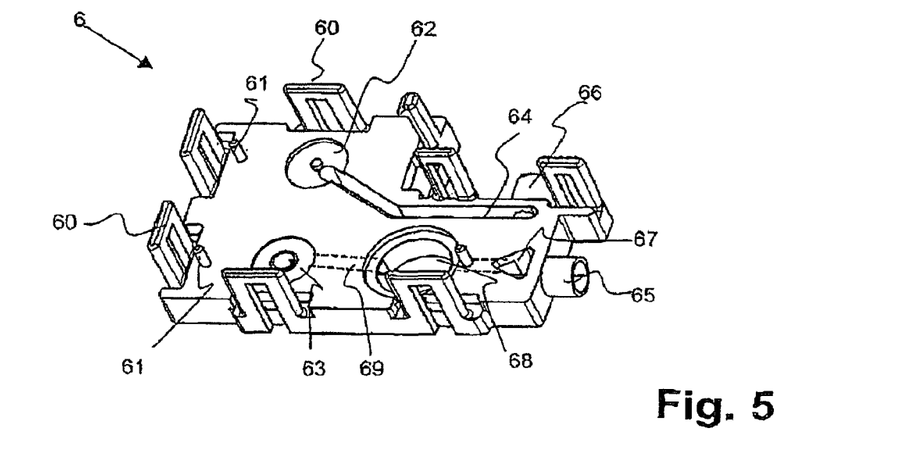
FIG. 5 shows a perspective view of a lower housing part of the suction pump according to FIG. 1.

The lower housing part 6 is shown in FIG. 4, and in another perspective view in FIG. 5. It also has a plate-shaped design, its underside forming the base of the pump assembly. The lower locking clips 60 project upward at the sides, such that the lower catches 41 of the middle housing part 4 can lock into them. Centering pins 61 are also present which also project upward and can be guided through the centering holes 30, 42, 50 of the membrane plate 3, of the middle housing part 4 and of the valve plate 5. These centering pins and centering holes make it easier to stack the individual levels on one another and thus permit rapid assembly.

The lower housing part 6 further comprises a first circular recess with central elevation, which forms an inlet opening 62. A second circular recess forms an outlet opening 63. This inlet opening 62 is connected to the vacuum channel 69 extending in the inside of the lower housing part 6. This channel 69 first passes through the safety valve opening 68 which is likewise designed as a trough and over which the safety membrane 55 of the first stage is arranged.

The connecting channel 64, open at the top and sealed off by the sealing lip 53, extends in the lower housing part 6 and opens into the outlet opening 63. This connecting channel 64 is connected to the second air release opening 67 present in the lower housing part 6.

As can be seen in FIG. 5, the connecting channel 64 ends in an exhaust attachment 66 which can be plugged into the exhaust 71. The second air release opening 67 leads to a breast shield attachment part 65, which is connected to the breast shield attachment piece 70.

This construction permits simple cleaning of the pump. If milk or another suctioned liquid gets into the pump, the latter can simply be flushed with water or air, the cleaning medium being pressed or blown in through the beast pump attachment piece 70 and leaving the pump again by way of the air release channel 72 and the exhaust 71.

Figure 9:
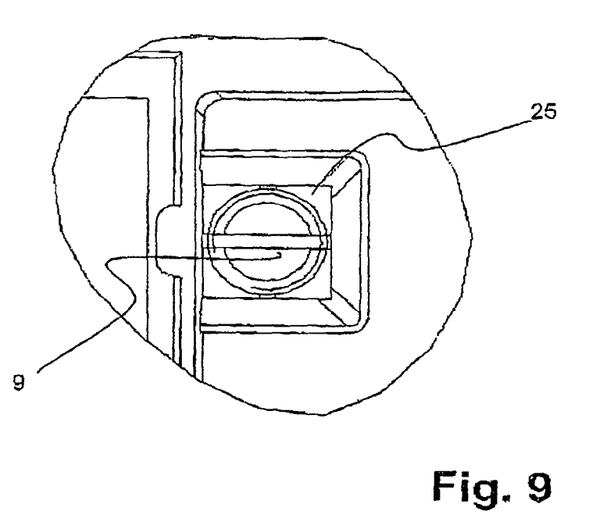
FIG. 9 shows a view into a part of the upper housing part from above.

FIG. 9 shows a partial view from above into the upper housing part 2. As can be seen here, the adjusting screw 9 of the safety valve S is designed with a round cross section but is screwed into a square thread opening 25. This means that a sufficient passage of air is at all times ensured.

Figure 10:
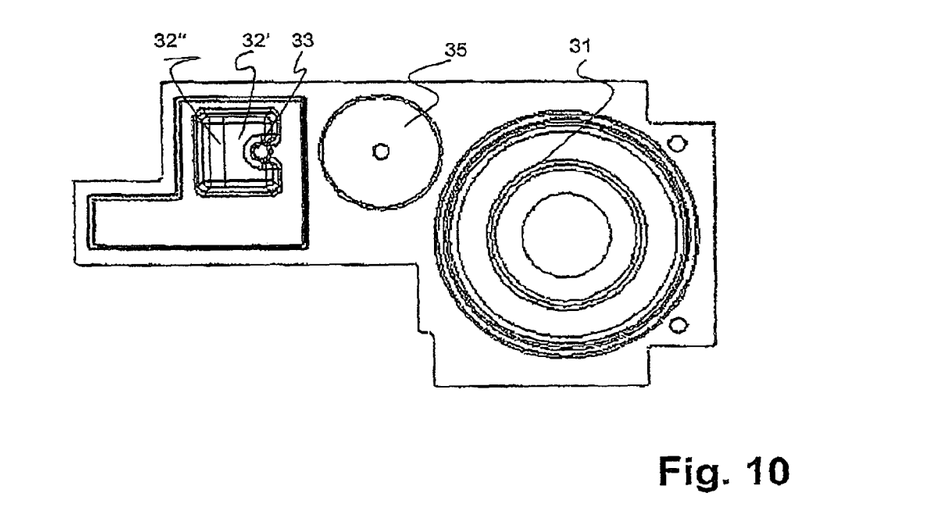
FIG. 10 shows a view of a membrane plate of the suction pump according to a second embodiment from above.
Figures 11, 12:
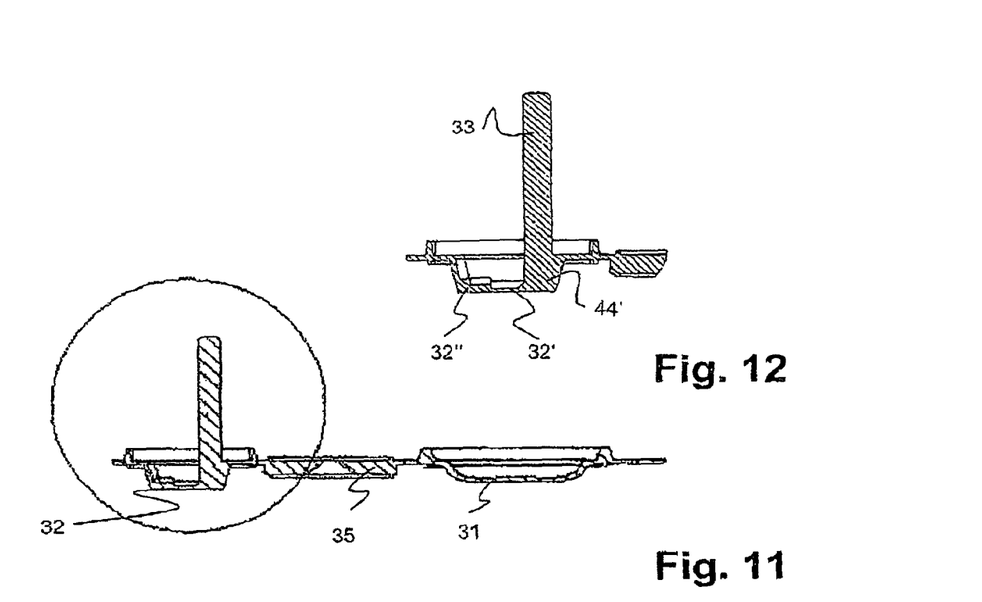
FIG. 11 shows a longitudinal section through the membrane plate according to FIG. 10.
FIG. 12 shows an enlarged detail of the membrane plate according to FIG. 11.

FIGS. 10 to 12 show a second embodiment. This embodiment differs from the one described above in the area of the air release valve. The other parts are of the same design and are therefore not described again here. In this example, the air release membrane 32 is not triangular, but square. However, it can also be hexagonal or octagonal or of any desired polygonal shape. It has been found in practice, however, that the square shape closes and opens more reliably compared to the triangular shape. The air release membrane is once again divided into thick and thin subsidiary areas 32', 32", the connecting pin 33 being arranged on the thin subsidiary area 32'. The two subsidiary areas 32', 32" are also substantially square, the connecting pin 33 being arranged on a long side of the thin subsidiary area 32' directed away from the thick subsidiary area 32". It is now no longer secured in a corner, but approximately midway along this long side, as can be seen in FIG. 10. It has also been found that the functionality is better ensured if the connecting pin is integrally formed on the side wall 44" of the chamber 44', as is shown in FIG. 12. However, the opening lying below this, that is to say the air release membrane seat 44, is preferably triangular as before. In this case, the connecting pin 33 is preferably arranged exactly over the corner of the triangular hole 44.

Figure 13:
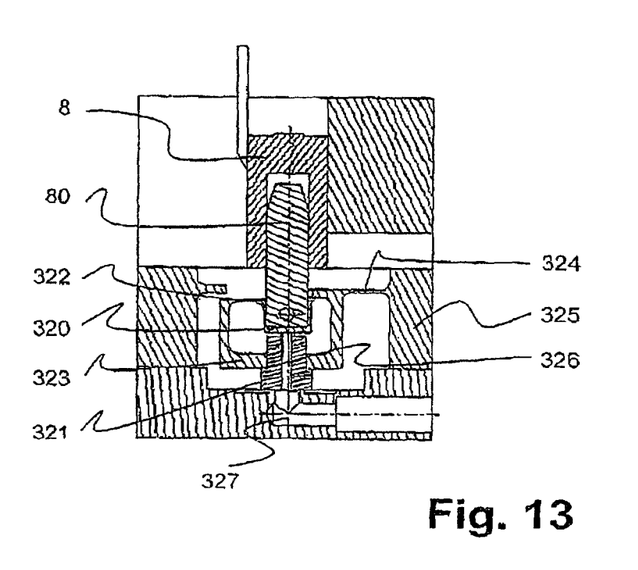
FIG. 13 shows a longitudinal section through an air release unit according to the invention in a third embodiment.

FIG. 13 shows a further embodiment of the air release valve according to the invention. The rest of the pump can be designed the same way as described above and is therefore not shown again here. The air release body is not a membrane here, but instead is formed by first and second air release blocks 320, 321.

The first air release block 320 is fixedly connected to the armature 80 of the lifting magnet 8. It is connected to the second air release block 321 via a first, soft spring element 322 and a retaining clip 323. The retaining clip 323 is secured, via a second, harder spring element 324, on a base body 325 surrounding the air release body. The base body 325, the first air release block 320, the retaining clip 323 and the two spring elements 322, 324 are preferably made of plastic and are all designed together in one piece.

The second air release block 321 has a first air release channel 326, which can be closed by the first air release block 320. The second air release block 321 closes a second air release channel 327, which is connected to the vacuum channel 69. The second air release channel 327 has a greater diameter than the first air release channel 326.

If the armature 80 of the magnet 8 is now lifted, the soft spring element 322 means that only the first air release block 320 is lifted at first and the first air release channel 326 is freed. If the armature 80 is lifted further, the magnet is then more powerful and, despite the harder spring element 324, is able to lift the second air release block 321 and thus free the second air release channel 327. A connection is thereby created now between the first air release channel 326 and the vacuum channel 69, and the underpressure in the pump is reduced. As an alternative or in addition to the springs of different strength, abutment elements can be provided which limit the travel of the first and second springs.

Therefore, in this embodiment too, the air release body is lifted such that it at first only frees part of the air release opening, with the result that less force is needed at the beginning of the lifting movement than at the end of the movement.

The suction pump according to the invention therefore affords several advantages. It provides wide-ranging functionality within a very small space and can also be produced inexpensively and is easy to assemble.

The invention claimed is:

1. A suction pump for generating a vacuum, the suction pump having:
a valve plate, a vacuum membrane which generates the vacuum, and an air release valve, the air release valve having an air release opening, an air release body which can close the air release opening sealingly, and an actuating means for actuating the air release body,
wherein the air release body is an air release membrane, wherein the actuating means is an electromagnet being connected with the air release membrane, and wherein the electromagnet lifts the air release membrane away from the valve plate in such a way that, upon opening of the air release valve, the air release membrane first frees only a partial area of the air release opening and thereafter frees a larger partial area or the air release opening in its entirety.

2. The suction pump as claimed in claim 1, the suction pump comprising an exhaust, a vacuum attachment and an air release attachment which protrude from an outer housing of the suction pump.

3. The suction pump as claimed in claim 1, wherein the air release membrane has an edge area which is first removed from the air release opening upon the opening of the air release valve.

4. The suction pump as claimed in claim 3, wherein the air release membrane is connected to an armature of the electromagnet via a connecting pin, and the connecting pin is connected to the edge area of the air release membrane.

5. The suction pump as claimed in claim 4, wherein the connecting pin is arranged over a corner of the air release opening.

6. The suction pump as claimed in claim 4, wherein the connecting pin is integrally formed with the air release membrane.

7. The suction pump as claimed in claim 4, wherein the connecting pin is arranged perpendicular to the air release membrane.

8. The suction pump as claimed in claim 3, wherein the air release membrane is made of silicon.

9. The suction pump as claimed in claim 3, wherein the air release membrane has at least one corner, and the edge area of the air release membrane comprises at least one of the at least one corner.

10. The suction pump as claimed in claim 3, wherein the air release membrane has a polygonal basic shape.

11. The suction pump as claimed in claim 3, wherein the air release membrane is substantially plane.

12. A method for operating a suction pump for generating a vacuum, the suction pump having:
a valve plate, a vacuum membrane which generates the vacuum, and an air release valve with an air release body, the air release body being an air release membrane which frees an air release opening at cyclical time intervals and thereafter closes it sealingly again, wherein the suction pump further comprises an electromagnet for actuating the air release membrane, the electromagnet being connected with the air release membrane,
wherein the electromagnet lifts the air release membrane away from the valve plate in such a way that the air release membrane at first frees only a partial area of the air release opening and thereafter frees a larger partial area or the air release opening in its entirety.

13. The method as claimed in claim 12, wherein the electromagnet at first removes the air release membrane from the air release opening at an edge area.

14. The method as claimed in claim 13, wherein the electromagnet at first removes the air release membrane at a corner of the air release opening.

15. A suction pump with a vacuum membrane used to generate a vacuum and an air release valve with an air release opening, wherein the air release valve has an air release membrane which closes the air release opening, and wherein the air release membrane and the vacuum membrane are designed integrally in the form of a common membrane plate, wherein the air release membrane is located at a distance to the vacuum membrane, wherein the suction pump comprises an upper housing part which receives a lifting magnet for actuating the air release membrane and receives an electric motor for actuating the vacuum membrane, a middle housing part with an air release membrane seat which is provided for the air release membrane and which surrounds the air release opening, and with a vacuum membrane seat for the vacuum membrane, and a lower housing part for forming a vacuum channel between the air release opening and an inlet opening of the vacuum membrane seat, the common membrane plate being arranged between the upper and middle housing parts, and a valve plate being arranged between the middle and lower housing parts.

16. The suction pump according to claim 15, wherein a part of the common membrane plate is designed as a safety membrane of a safety valve.

17. The suction pump according to claim 15, wherein the valve plate and the common membrane plate are substantially plane.

18. The suction pump according to claim 15, wherein the valve plate and the common membrane plate are made of silicone.

19. The suction pump according to claim 15, the suction pump comprising an exhaust, a vacuum connecting element and an air release connecting element which protrude from an outer housing of the suction pump.

20. The suction pump according to claim 19, wherein an exhaust connecting element is formed integrally on the lower housing part and can be connected to the exhaust formed integrally on a connecting part.

* * * * *

UNITED STATES PATENT AND TRADEMARK OFFICE
CERTIFICATE OF CORRECTION

Page 1 of 1

PATENT NO. : 9,644,622 B2
APPLICATION NO. : 13/936064
DATED : May 9, 2017
INVENTOR(S) : Alex Stutz et al.

It is certified that error appears in the above-identified patent and that said Letters Patent is hereby corrected as shown below:

On the Title Page

At item (63) (Related U.S. Application Data), after "11/662,683" delete "filed on Mar. 12, 2007" and insert --filed as a national stage application of International application no. PCT/CH05/00529 filed on September 6, 2005--

Signed and Sealed this
Ninth Day of January, 2018

Joseph Matal
*Performing the Functions and Duties of the*
*Under Secretary of Commerce for Intellectual Property and*
*Director of the United States Patent and Trademark Office*